(12) United States Patent
Hashimoto et al.

(10) Patent No.: US 10,813,709 B2
(45) Date of Patent: Oct. 27, 2020

(54) ROBOT SYSTEM

(71) Applicant: KAWASAKI JUKOGYO KABUSHIKI KAISHA, Kobe-shi, Hyogo (JP)

(72) Inventors: Yasuhiko Hashimoto, Kobe (JP); Masayuki Kamon, Akashi (JP)

(73) Assignee: KAWASAKI JUKOGYO KABUSHIKI KAISHA, Kobe-Shi (JP)

( * ) Notice: Subject to any disclaimer, the term of this patent is extended or adjusted under 35 U.S.C. 154(b) by 312 days.

(21) Appl. No.: 15/755,213

(22) PCT Filed: May 27, 2016

(86) PCT No.: PCT/JP2016/002584
§ 371 (c)(1),
(2) Date: Feb. 26, 2018

(87) PCT Pub. No.: WO2017/033357
PCT Pub. Date: Mar. 2, 2017

(65) Prior Publication Data
US 2018/0250814 A1 Sep. 6, 2018

(30) Foreign Application Priority Data
Aug. 25, 2015 (JP) .................................. 2015-165479

(51) Int. Cl.
*B25J 9/16* (2006.01)
*A61B 34/37* (2016.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC . G06T 7/70; G06T 7/62; H04N 7/181; H04N 5/23219; G06F 3/017; B25J 9/1646;
(Continued)

(56) References Cited

U.S. PATENT DOCUMENTS 5,570,458 A   10/1996  Umeno et al.
2004/0189631 A1*  9/2004  Kazi ..................... B25J 9/1671
                                                            345/418
(Continued)

FOREIGN PATENT DOCUMENTS

CN   104057453 A    9/2014
EP   1145804 A1   10/2001
(Continued)

OTHER PUBLICATIONS

Jul. 26, 2016 International Search Report issued in International Patent Application No. PCT/JP2016/002584.

*Primary Examiner* — Adam R Mott
(74) *Attorney, Agent, or Firm* — Oliff PLC (57) ABSTRACT

A robot system includes a robotic arm having an end effector configured to perform a work to a work object, a memory part storing information that causes the end effector to move as scheduled route information, a motion controller configured to operate the robotic arm by using the scheduled route information to move the end effector, a route correcting device configured to generate, by being manipulated, manipulating information to correct a route of the end effector during movement, a camera configured to image the work object, an image generator configured to generate a synthesized image by synthesizing a scheduled route of the end effector obtained from the scheduled route information with a captured image sent from the camera, and a monitor configured to display the synthesized image.

4 Claims, 5 Drawing Sheets

(51) Int. Cl.
| | |
|---|---|
| G05B 19/418 | (2006.01) |
| B25J 9/00 | (2006.01) |
| B23P 19/04 | (2006.01) |
| B25J 13/00 | (2006.01) |
| B25J 19/04 | (2006.01) |
| B25J 13/08 | (2006.01) |
| B25J 3/00 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . B25J 3/00 (2013.01); B25J 3/04 (2013.01); B25J 9/0081 (2013.01); B25J 9/0084 (2013.01); B25J 9/0087 (2013.01); B25J 9/161 (2013.01); B25J 9/1602 (2013.01); B25J 9/163 (2013.01); B25J 9/1612 (2013.01); B25J 9/1628 (2013.01); B25J 9/1633 (2013.01); B25J 9/1646 (2013.01); B25J 9/1653 (2013.01); B25J 9/1664 (2013.01); B25J 9/1669 (2013.01); B25J 9/1674 (2013.01); B25J 9/1682 (2013.01); B25J 9/1689 (2013.01); B25J 9/1697 (2013.01); B25J 11/008 (2013.01); B25J 13/00 (2013.01); B25J 13/003 (2013.01); B25J 13/006 (2013.01); B25J 13/02 (2013.01); B25J 13/025 (2013.01); B25J 13/06 (2013.01); B25J 13/065 (2013.01); B25J 13/08 (2013.01); B25J 13/084 (2013.01); B25J 13/085 (2013.01); B25J 13/087 (2013.01); B25J 13/088 (2013.01); B25J 18/00 (2013.01); B25J 19/023 (2013.01); B25J 19/028 (2013.01); B25J 19/04 (2013.01); G05B 19/4182 (2013.01); G06F 3/017 (2013.01); G06T 7/62 (2017.01); G06T 7/70 (2017.01); H04N 5/23219 (2013.01); H04N 7/181 (2013.01); B23P 21/00 (2013.01); B23P 21/002 (2013.01); G05B 2219/33007 (2013.01); G05B 2219/35464 (2013.01); G05B 2219/37297 (2013.01); G05B 2219/39004 (2013.01); G05B 2219/39102 (2013.01); G05B 2219/39439 (2013.01); G05B 2219/39531 (2013.01); G05B 2219/39533 (2013.01); G05B 2219/40022 (2013.01); G05B 2219/40134 (2013.01); G05B 2219/40136 (2013.01); G05B 2219/40139 (2013.01); G05B 2219/40142 (2013.01); G05B 2219/40143 (2013.01); G05B 2219/40145 (2013.01); G05B 2219/40146 (2013.01); G05B 2219/40161 (2013.01); G05B 2219/40162 (2013.01); G05B 2219/40163 (2013.01); G05B 2219/40169 (2013.01); G05B 2219/40182 (2013.01); G05B 2219/40183 (2013.01); G05B 2219/40195 (2013.01); G05B 2219/40387 (2013.01); G05B 2219/40627 (2013.01); Y10S 901/02 (2013.01); Y10S 901/03 (2013.01); Y10S 901/08 (2013.01); Y10S 901/09 (2013.01); Y10S 901/10 (2013.01); Y10S 901/27 (2013.01); Y10S 901/41 (2013.01); Y10S 901/46 (2013.01); Y10S 901/47 (2013.01)

(58) Field of Classification Search
CPC ...... B25J 9/0081; B25J 13/087; B25J 13/085; B25J 9/1602; B25J 19/028; B25J 9/1612; B25J 9/1674; B25J 9/1653; B25J 13/084; B25J 13/025; B25J 13/065; B25J 13/003; B25J 11/008; B25J 9/163; B25J 13/02; B25J 9/1628; B25J 9/1633; B25J 3/04; B25J 19/023; B25J 9/1689; B25J 9/1682; B25J 9/1664; B25J 9/161; B25J 18/00; B25J 13/088; B25J 13/06; B25J 9/1669; B25J 3/00; B25J 9/0087; B25J 13/08; B25J 13/006; B25J 9/1697; B25J 9/0084; B25J 19/04; B25J 13/00; B25J 9/126; B25J 19/06; B25J 19/02; B25J 11/005; B25J 9/1692; B25J 9/1661; B25J 9/1605; B25J 9/1666; B25J 9/1676; B25J 9/1671; B25J 13/04; B23Q 15/12; B23P 19/04; B23P 21/002; B23P 21/00; G05B 19/4182; G05B 2219/40136; G05B 2219/40162; G05B 2219/40195; G05B 2219/40134; G05B 2219/40183; G05B 2219/40169; G05B 2219/33007; G05B 2219/40142; G05B 2219/35464; G05B 2219/39533; G05B 2219/40163; G05B 2219/39531; G05B 2219/40022; G05B 2219/39439; G05B 2219/40627; G05B 2219/40146; G05B 2219/40161; G05B 2219/40139; G05B 2219/40387; G05B 2219/40145; G05B 2219/40182; G05B 2219/39004; G05B 2219/40143; G05B 2219/39102; G05B 2219/37297; G05B 2219/10091; G05B 2219/40167; G05B 2219/40168; Y10S 901/02; Y10S 901/46; Y10S 901/10; Y10S 901/41; Y10S 901/27; Y10S 901/03; Y10S 901/08; Y10S 901/47; Y10S 901/09; A61B 34/37; A61B 34/32; A61B 34/70; A61B 34/35
See application file for complete search history.

(56) References Cited

U.S. PATENT DOCUMENTS

| | | | |
|---|---|---|---|
| 2013/0218340 A1* | 8/2013 | Hager | B25J 9/1671 700/257 |
| 2014/0277737 A1 | 9/2014 | Sekiyama et al. | |

FOREIGN PATENT DOCUMENTS

| | | |
|---|---|---|
| JP | S56-39884 A | 4/1981 |
| JP | 2003-311661 A | 11/2003 |
| JP | 2011-224696 A | 11/2011 |
| JP | 2013-071231 A | 4/2013 |
| JP | 2014-065100 A | 4/2014 |

* cited by examiner

FIG. 5

ROBOT SYSTEM

TECHNICAL FIELD

The present disclosure relates to a robot system.

BACKGROUND ART

Conventionally, an iterative work, such as welding, painting, assembling of components, or applicating of seal adhesive, is automatically performed in a manufacture site by an industrial robot. In order to make the robot perform the work, the robot is necessary to be taught with information required for the work and to store the information therein. For example, Patent Document 1 discloses one example of the teaching a robotic arm to store a work route by direct teaching.

REFERENCE DOCUMENT OF CONVENTIONAL ART

Patent Document

[Patent Document 1] JP2013-071231A

DESCRIPTION OF THE DISCLOSURE

Problems to be Solved by the Disclosure

The robot is capable of achieving the repeating of the same work at high speed and with high accuracy based on the taught information. However, when a work object varies or a work environment changes, quality of work may not be able to be secured with the same route. Meanwhile, in a master-slave type robot system, some systems are configured so that, when the operator manually operates or manipulates a master arm, a slave arm operates so as to follow or trace that operation. The work performed by such a system may be flexibly performed by the slave arm as the operator manipulates the master arm for each work object, but, on the contrary, the work requires significant time and labors.

Therefore, the present disclosure provides a robot system, which is flexibly adaptable to each work and is reducible of operator's labors.

SUMMARY OF THE DISCLOSURE

In order to solve the problem, the present inventors thought about a system in which an operator manipulates a device capable of remotely controlling a robotic arm while the robotic arm is operating automatically based on a preset program, to correct a route of the robotic arm by reflecting the manipulation in the correction. However, in this system, a suitable correction cannot be achieved unless the operator is able to grasp in advance how the preset route of the robotic arm is to be corrected. The present disclosure is made in view of such an aspect.

That is, a robot system according to the present invention includes a robotic arm having an end effector configured to perform a work to a work object, a memory part storing information that causes the end effector to move as scheduled route information, a motion controller configured to operate the robotic arm by using the scheduled route information to move the end effector, a route correcting device configured to generate, by being manipulated, manipulating information to correct a route of the end effector during movement, a camera configured to image the work object, an image generator configured to generate a synthesized image by synthesizing a scheduled route of the end effector obtained from the scheduled route information with a captured image sent from the camera, and a monitor configured to display the synthesized image.

With this configuration, the synthesized image where the scheduled route of the end effector is synthesized with the captured image in which the work object is imaged by the image generator is displayed on the monitor. By this, an operator is able to grasp beforehand whether the end effector moves appropriately so as to perform a given work to the work object. In addition, since the route of the end effector during movement is correctable on real time by the route correcting device, the route of the end effector is corrected at a point where the route correction is necessary, while the operator looks at the synthesized image on the monitor. In this manner, the point where the route correction is necessary is recognizable from the synthesized image on the monitor and, thus, it is flexibly adaptable to each work, and since the route correction is able to be made by the manipulation only at the necessary part, the operator's labors can be reduced.

In the robot system, the image generator may acquire present positional information on the end effector, and update, based on the present positional information, the scheduled route of the end effector synthesized with the captured image. With this configuration, the scheduled route of the end effector after the route correction is made by the route correcting device is displayed on the monitor. Thus, the operator is able to grasp beforehand whether the end effector moves so as to perform the given work to the work object even after the route correction is made by the route correcting device.

In the robot system, the scheduled route of the end effector may be a first scheduled route that is a route of the end effector planned when the route correcting device is not manipulated from the present time point. The image generator may further synthesize with the captured image, a second scheduled route that is a route of the end effector planned when a state where the route correcting device is manipulated is maintained from the present time point. With this configuration, since the two scheduled routes when the route correcting device is not operated from the present time point and when the state where the route correcting device has been operated is maintained from the present time point, are indicated on the monitor, the operator is able to judge more accurately about how the route correcting device is to be manipulated.

In the robot system, the image generator may indicate a posture of the end effector when the end effector reaches a given position on the scheduled route, at the given position. With this configuration, it is possible to grasp beforehand whether the end effector takes the posture by which the end effector is capable of appropriately performing the work to the work object when the end effector traces the scheduled route.

Effect of the Disclosure

The present disclosure can provide a robot system capable of being flexibly adapted to each work and reducing the operator's labors.

MODE FOR CARRYING OUT THE DISCLOSURE

Hereinafter, a robot system according to one embodiment of the present disclosure is described with reference to the accompanying drawings. The robot system 100 according to this embodiment is a system including a robotic arm 1 which repeatedly performs a given work, and a manipulating device 2 which is capable of manipulating operation of the robotic arm 1 by manual operation. In the robot system 100, the operator who is located at a position distant from a workspace of the robotic arm 1 (outside of the workspace) manipulates the manipulating device 2 to input instructions so that the robotic arm 1 is capable of performing an operation corresponding to the instructions to perform a specific work. Moreover, in the robot system 100, the robotic arm 1 is also capable of automatically performing a given work, without the manipulation of the manipulating device 2 by the operator.

An operating mode in which the robotic arm 1 is operated according to the instructions inputted through the manipulating device 2 is herein referred to as a "manual mode." Note that the "manual mode" also includes a case where part of the operation of the robotic arm 1 under operation is automatically corrected based on the instructions inputted by the operator manipulating the manipulating device 2. Moreover, an operating mode in which the robotic arm 1 is operated according to a preset task program is referred to as an "automatic mode."

Further, the robot system 100 of this embodiment is configured so that the manipulation of the manipulating device 2 is reflectable in the automatic operation of the robotic arm 1 while the robotic arm 1 is operating automatically to correct the operation to be carried out automatically. An operating mode in which the robotic arm 1 is operated according to the preset task program while the instructions inputted through the manipulating device 2 is reflectable is herein referred to as a "correctable automatic mode." Note that the "automatic mode" described above is distinguished from the "correctable automatic mode" in that the manipulation of the manipulating device 2 is not reflected in the operation of the robotic arm 1 when the operating mode in which the robotic arm 1 is operated is the automatic mode.

Figure 1:
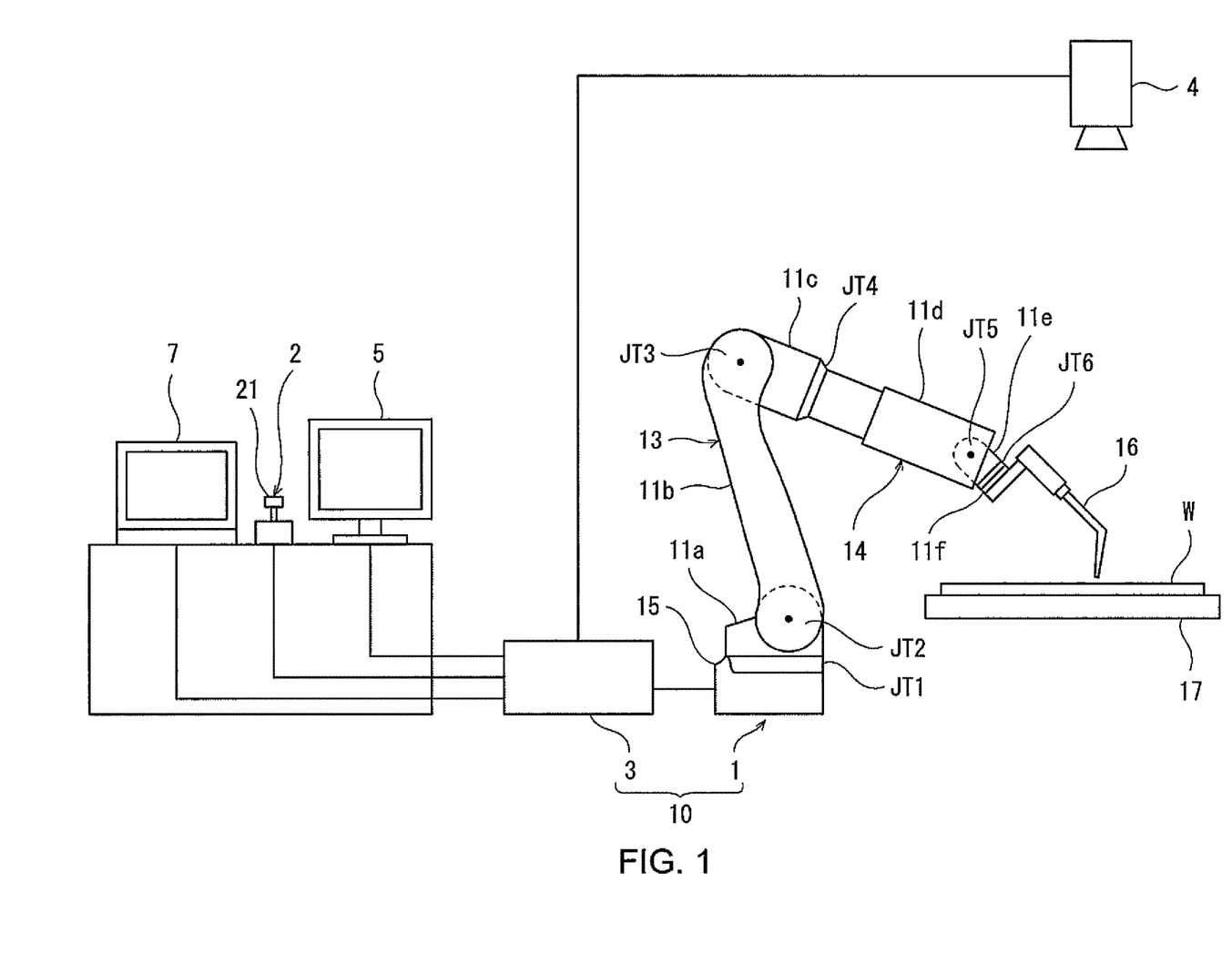
FIG. 1 is a schematic diagram illustrating a configuration of a robot system according to one embodiment.

First, with reference to FIG. 1, a configuration of the robot system 100 according to this embodiment is described. FIG. 1 is a schematic diagram illustrating one example of a configuration of the robot system 100 according to this embodiment. As illustrated in FIG. 1, the robot system 100 includes an industrial robot 10, the manipulating device 2, a camera 4, a monitor 5, and an input device 7. Below, each component of the robot system 100 is described in detail.

(Structure of Industrial Robot 10)

The industrial robot 10 includes the robotic arm 1, an end effector 16 attached to a tip end of the robotic arm 1, and a control device 3 which governs the operations of the robotic arm 1 and the end effector 16. In this embodiment, the industrial robot 10 is a welding robot which welds a work object (hereinafter, referred to as "the workpiece") W, and the end effector 16 is a welding torch. The workpiece W is comprised of, for example, two members to be mutually joined by welding, which are, for example, sheet metals. The industrial robot 10 includes a welder which supplies electricity and shielding gas to the welding torch, and a filler-material feeding device which feeds a wire-like filler material to a tip end of the welding torch (none of them is illustrated). The industrial robot 10 performs the welding work to the workpiece W set onto a table 17. Note that the industrial robot 10 is not limited in particular, and may be, for example, an assembly robot, a paint robot, an application robot, an inspection robot, etc.

The robotic arm 1 includes a pedestal 15, an arm part 13 supported by the pedestal 15, and a wrist part 14 which is supported by a tip end of the arm part 13 and to which the end effector 16 is attached. As illustrated in FIG. 1, the robotic arm 1 is an articulated robotic arm having a plurality of (three or more) joints JT1-JT6, and is constructed by serially coupling a plurality of links 11a-11f. In more detail, at the first joint JT1, the pedestal 15 and a base-end part of the first link 11a are rotatably coupled to each other about an axis extending vertically. At the second joint JT2, a tip-end part of the first link 11a and a base-end part of the second link 11b are rotatably coupled to each other about an axis extending horizontally. At the third joint JT3, a tip-end part of the second link 11b and a base-end part of the third link 11c are rotatably coupled to each other about an axis extending horizontally. At the fourth joint JT4, a tip-end part of the third link 11c and a base-end part of the fourth link 11d are rotatably coupled to each other about an axis extending in the longitudinal directions of the fourth link 11c. At the fifth joint JT5, a tip-end part of the fourth link 11d and a base-end part of the fifth link 11e are rotatably coupled to each other about an axis perpendicular to the longitudinal directions of the link 11d. At the sixth joint JT6, a tip-end part of the fifth link 11e and a base-end part of the sixth link 11f are twistably and rotatably coupled to each other. A mechanical interface is provided to a tip-end part of the sixth link 11f. The end effector 16 corresponding to the contents of work of the robotic arm 1 is attached to the mechanical interface attachably and detachably.

The arm part 13 of the robotic arm 1 is formed by a coupled body of the links and the joints, which is comprised of the first joint JT1, the first link 11a, the second joint JT2, the second link 1ib, the third joint JT3, and the third link 11c, described above. Moreover, the wrist part 14 of the robotic arm 1 is formed by a coupled body of the links and the joints, which is comprised of the fourth joint JT4, the fourth link 11d, the fifth joint JT5, the fifth link 11e, the sixth joint JT6, and the fourth link 11f, described above.

The joints JT1-JT6 are provided with drive motors M1-M6 (see FIGS. 2 and 3) as one example of an actuator which relatively rotates two members connected by each joint. The drive motors M1-M6 are, for example, servo motors which are servo-controlled by the control device 3. Moreover, the joints JT1-JT6 are provided with rotation sensors E1-E6 (see FIGS. 2 and 3) for detecting rotational positions of the drive motors M1-M6, and current sensors C1-C6 (see FIG. 3) for detecting current which control the rotations of the drive motors M1-M6, respectively. The rotation sensors E1-E6 are, for example, encoders. Note that in the description of the drive motors M1-M6, the rotation sensors E1-E6, and the current sensors C1-C6, 1-6 of suffixes are given to the alphabets corresponding to the respective joints JT1-JT6. Below, when an arbitrary joint is illustrated among the joints JT1-JT6, the suffix is omitted and the joint is referred to as "JT," and the same is applied to the drive motor M, the rotation sensor E, and the current sensor C.

The control device 3 is comprised of, for example, an arithmetic part (not illustrated), such as a micro controller, an MPU or a PLC (Programmable Logic Controller), a logic circuit, and a memory part (not illustrated), such as a ROM or a RAM.

Figure 2:
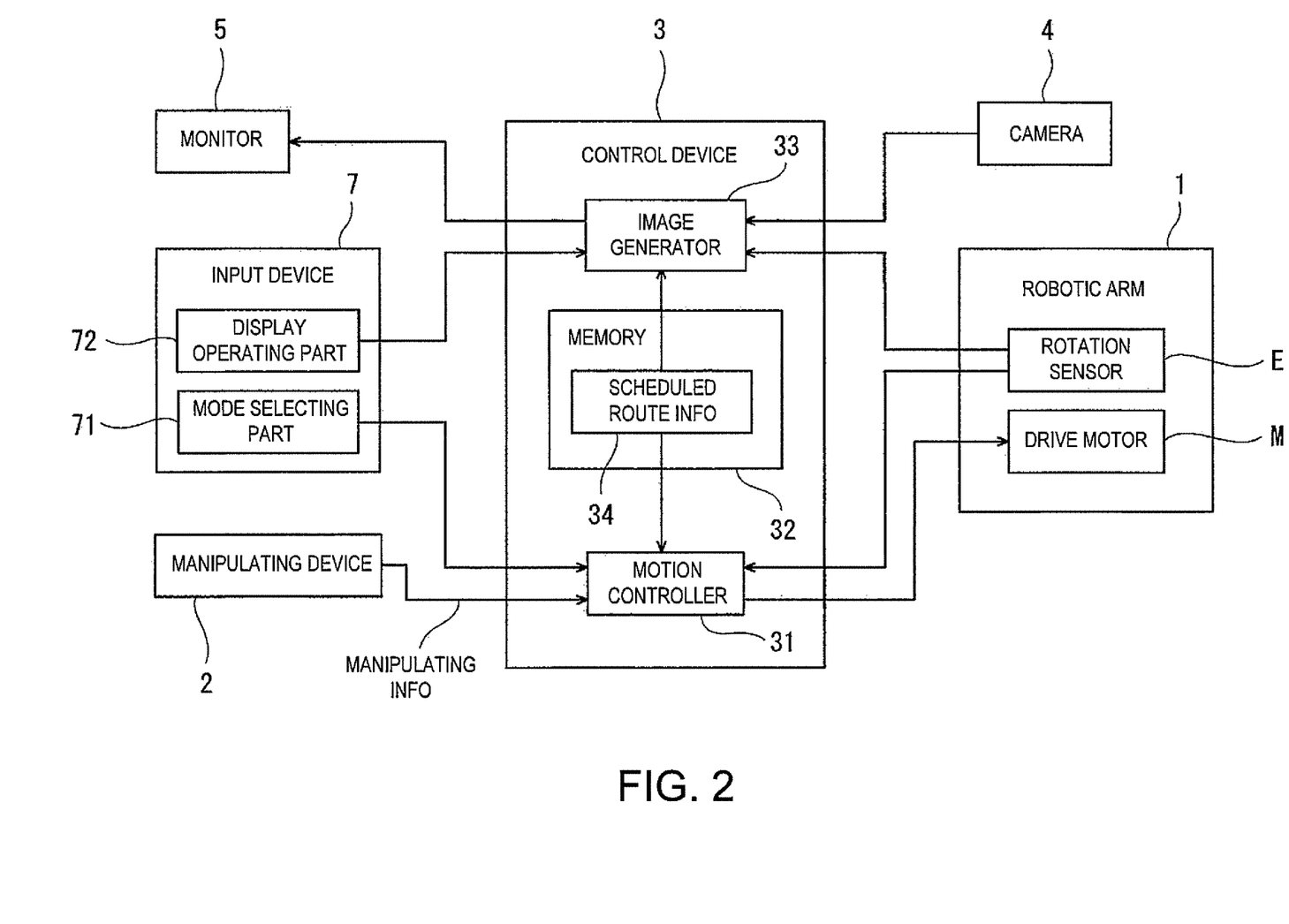
FIG. 2 is a schematic diagram illustrating a configuration of a control system of the robot system illustrated in FIG. 1.

FIG. 2 is a schematic diagram illustrating a configuration of a control system of the robot system 100. Note that, in FIG. 2, for simplification, one drive motor M and one rotation sensor E are illustrated, and the current sensor C is omitted. As illustrated in FIG. 2, the control device 3 includes a motion controller 31, a memory part 32, and an image generator 33 as functional blocks. For example, the functional blocks provided to the control device 3 is implementable by the arithmetic part of the control device 3 reading and executing the program stored in the memory part.

The memory part 32 stores information for causing the end effector 16 to move automatically, as scheduled route information 34. The scheduled route information 34 is, for example, teaching information which is stored by operating the robotic arm 1 to perform a given work according to teaching. The scheduled route information 34 may be route information containing time-series data, or may be path information indicative of pauses at discontinuous points. Note that, in the robot system 100 according to this embodiment, the memory part 32 is provided to the control device 3, but may be provided separately from the control device 3. The motion controller 31 controls the operation of the robotic arm 1. Details of the motion controller 31 and the image generator 33 will be described later.

(Manipulating Device 2)

Returning to FIG. 1, the manipulating device 2 is a device which receives a manipulating instruction from the operator. The manipulating device 2 is installed outside the workspace of the robotic arm 1. The manipulating device 2 has a manipulating part 21 which is manually operated or manipulated by the operator. The manipulating device 2 in this embodiment is, for example, a joystick, while the manipulating part 21 is a pivotable-type control lever. Manipulating information is generated by manipulating the manipulating part 21 of the manipulating device 2. The manipulating information contains information related to an amount and a direction of manipulation of the manipulating part 21. In this embodiment, the amount of manipulation of the manipulating part 21 is an amount of tilting operation of the control lever, and the direction of manipulation of the manipulating part 21 is a direction of the tilting operation of the control lever. The generated manipulating information is sent to the control device 3.

In the robot system 100 of this embodiment, when the manipulating information is sent to the control device 3 while the operating mode in which the robotic arm 1 is operated is the manual mode, the robotic arm 1 performs operation according to the manipulating information, i.e., according to the amount and direction of manipulation of the manipulating part 21. Moreover, when the manipulating information is sent to the control device 3 while the operating mode in which the robotic arm 1 is operated is the correctable automatic mode, the route of the robotic arm 1 which is operating automatically is corrected according to the manipulating information, i.e., according to the amount and direction of manipulation of the manipulating part 21. In this embodiment, the manipulating device 2 functions as a route correcting device which corrects the route of the end effector 16 during movement, as will be described later.

The manipulating part 21 is configured, when the operator leaves his/her hand from the manipulating part 21, to return to a neutral state where it is not operated in any direction, by a biasing member, such as a spring. Below, a state where the manipulating part 21 is operated by the operator (i.e., a state where the manipulating part 21 is not at the neutral) is referred to as "the manipulating state" of the manipulating device 2, and a state where the manipulating part 21 is not operated by the operator (i.e., a state where the manipulating part 21 is at the neutral) is referred to as "the non-manipulated state" of the manipulating device 2. Note that the manipulating part 21 may not be configured to return to the neutral state when the operator leaves his/her hand from the manipulating part 21, but, for example, the manipulating part 21 may be configured to maintain the state before the operator leaves his/her hand from the manipulating part 21. In this case, even when the operator has left his/her hand from the manipulating part 21, the manipulating part 21 is considered to be operated unless the manipulating part 21 is in the neutral state.

(Camera 4 and Monitor 5)

The camera 4 images or captures images of the workpiece W and the end effector 16 which performs the given work to the workpiece W. The camera 4 is installed in the space where the robotic arm 1 is provided. The camera 4 is set so that an image captured by the camera contains the workpiece W and a tip-end part of the end effector 16 (the tip-end part of the welding torch) which directly acts on the workpiece W. In more detail, the camera 4 is set at a position where it is recognizable of a working part of the workpiece W, and a route of the end effector 16 which performs the work to the workpiece W. In this embodiment, although the camera 4 is provided to image the workpiece W from above, but it is not limited in particular, and it may be provided to image the workpiece W from obliquely upward. For example, when the working part of the workpiece W set on the table 17 extends vertically, and the end effector 16 performs the work to the workpiece W while moving vertically, the camera 4 may be set so as to image the workpiece W from sideway. Moreover, in this embodiment, the camera 4 is provided so that its relative position with respect to the workpiece W set on the table 17 may be fixed.

The camera 4 is connected with the control device 3. The camera 4 and the control device 3 may be connected with each other wiredly or wirelessly.

The captured image which is captured by the camera 4 is sent to the image generator 33 of the control device 3. Moreover, the scheduled route information 34 is also sent to the image generator 33 from the memory part 32. The image generator 33 generates a synthesized image which is obtained by synthesizing a scheduled route of the end effector 16 acquired from the scheduled route information 34 with the captured image sent from the camera 4. In more detail, the image generator 33 uses the captured image sent from the camera 4 as the background, and superimposes the scheduled route of the tip-end part of the end effector 16 on the captured image.

Moreover, the image generator 33 acquires the present positional information of the end effector 16 in the captured image, and updates the scheduled route of the end effector 16 which is synthesized with the captured image, based on the present positional information. In this embodiment, the image generator 33 calculates the present position in the captured image based on the rotational position information of each drive motor M sent from the rotation sensor E. Note that the method of acquiring the present positional information may be any kind of method, and, for example, the image generator 33 may acquire the present positional information from the motion controller 31.

In this embodiment, the image generator 33 synthesizes two scheduled routes of a first scheduled route $L_1$ and a second scheduled route $L_2$, with the captured image.

The first scheduled route $L_1$ is a route where the end effector 16 is scheduled to trace when the state of the manipulating device 2 at the present time point is in the non-manipulated state. In other words, the first scheduled route $L_1$ is the route of the end effector 16 which is planned when the manipulating device 2 is not operated from the present time point. The first scheduled route $L_1$ is generated by the image generator 33 based on the scheduled route information 34 sent from the memory part 32 and the present positional information of the end effector 16.

Moreover, the second scheduled route $L_2$ is a route where the end effector 16 is scheduled to trace when the manipulating state of the manipulating device 2 (including the amount and direction of manipulation of the manipulating part 21) at the present time point is maintained. In other words, the second scheduled route $L_2$ is the route of the end effector 16 which is planned when the state where the manipulating device 2 is being manipulated is maintained from the present time point. The second scheduled route $L_2$ is generated by the image generator 33 based on the scheduled route information 34 sent from the memory part 32, the present positional information of the end effector 16, and the manipulating information sent at the present time point.

When the manipulating device 2 is currently in the non-manipulated state, the second scheduled route $L_2$ is the same as the first scheduled route $L_1$. Thus, the image generator 33 synthesizes only the first scheduled route $L_1$ on the captured image in order to avoid duplication.

The first and second scheduled routes $L_1$ and $L_2$ which are synthesized with the captured image may be any kind of forms, as long as the operator is visually recognizable of them. For example, as for the first and second scheduled routes $L_1$ and $L_2$ in the synthesized image, lines along which a representative point is expected to trace in the captured image based on the scheduled route information 34 may be expressed by solid lines, dashed lines, etc., where the representative point is the tip-end part of the end effector 16. In this embodiment, the image generator 33 displays, in the captured image, the first scheduled route $L_1$ by a thin dashed line, and the second scheduled route $L_2$ by a thick dashed line.

Moreover, the image generator 33 synthesizes a posture image which is an image indicative of the posture of the end effector 16, with the captured image. Specifically, the image generator 33 indicates the posture of the end effector 16 when the end effector 16 reaches a given position on the scheduled route, at the given position. In this embodiment, a posture image $P_1$ of the end effector 16 when the end effector 16 reaches a given position on the first scheduled route $L_1$1 is synthesized at the given position of the captured image. Moreover, a posture image $P_2$ of the end effector 16 when the end effector 16 reaches a given position on the second scheduled route $L_2$ is synthesized at the given position of the captured image.

Here, "the given position of the scheduled route" where the posture image of the end effector 16 is displayed is not limited in particular, and, for example, it may be a scheduled position of the end effector 16 when the end effector 16 moves along the scheduled route from the present position by a given distance, or may be a scheduled position of the end effector 16 when a given period of time is passed from the present time point. Moreover, the posture images $P_1$ and $P_2$ may include a plurality of posture images, respectively. For example, the plurality of posture images $P_1$ may be synthesized with the captured image so as to be spaced from each other along the first scheduled route $L_1$.

The images $P_1$ and $P_2$ indicative of the postures of the end effector 16 may be any kind of forms, as long as they indicate the orientation of the end effector 16 with respect to the workpiece W, and for example, they may be arrow-shaped indications with respect to the workpiece W, or may be symbols or graphic figures which imitate the end effector 16. Alternatively, the images $P_1$ and $P_2$ indicative of the postures of the end effector 16 may be actually-captured images of the end effector 16 imaged by a camera other than the camera 4. In this embodiment, the images $P_1$ and $P_2$ indicative of the postures of the end effector 16 schematically indicate the tip-end part of the welding torch which is the end effector 16, and they indicate the orientations of the welding torch with respect to the workpiece W when the welding torch is seen from the moving direction of the welding torch.

Note that, in the robot system 100 according to this embodiment, although the image generator 33 is provided to the control device 3, it may be provided separately from the control device 3.

The control device 3 is connected with the monitor 5, and the synthesized image generated by the image generator 33 is sent and outputted to the monitor 5. The monitor 5 and the control device 3 may be connected with each other wiredly or wirelessly. The monitor 5 is installed in the space where the manipulating device 2 is provided. The operator compares the part of the workpiece W to be worked with the scheduled route of the tip-end part of the end effector 16, while looking at the synthesized image outputted to the monitor 5, and manipulates the manipulating device 2 so that the appropriate work is performed to the workpiece W.

(Input Device 7)

The input device 7 is an input device which is installed outside the workspace, together with the manipulating device 2, receives the manipulating instruction from the operator, and inputs the received manipulating instruction into the control device 3. In this embodiment, although the input device 7 is a computer, but it is not limited in particular, and for example, may be a switch, an adjustment knob, a control lever, or a mobile terminal, such as a tablet computer.

As illustrated in FIG. 2, the input device 7 includes a mode selecting part 71 and a display operating part 72. The mode selecting part 71 is used by the operator to select the operating mode in which the robotic arm 1 is operated, from the automatic mode, the correctable automatic mode, and the manual mode, which are described above. Information related to the operating mode selected in the mode selecting part 71 is sent to the motion controller 31 of the control device 3. The motion controller 31 causes the robotic arm 1 to operate based on the information sent from the mode selecting part 71, i.e., according to the operating mode selected by the mode selecting part 71.

Specifically, the scheduled route information 34 stored in the memory part 32 is sent to the motion controller 31 as information for operating the robotic arm 1 automatically. Moreover, the manipulating information generated by manipulating the manipulating device 2 is sent to the motion controller 31. The motion controller 31 uses one or both of the scheduled route information 34 and the manipulating information according to the operating mode selected in the mode selecting part 71.

When the operating mode selected in the mode selecting part 71 is the manual mode, the motion controller 31 uses the manipulating information. In more detail, when the operating mode in which the robotic arm 1 is operated is the manual mode, the motion controller 31 controls the operation of the robotic arm 1 using the manipulating information (inputted instructions) sent by manipulating the manipulating device 2, without using the scheduled route information 34 sent from the memory part 32.

Moreover, when the operating mode selected in the mode selecting part 71 is the automatic mode, the motion controller 31 uses the scheduled route information 34. In more detail, when the operating mode in which the robotic arm 1 is operated is the automatic mode, the motion controller 31 controls the operation of the robotic arm 1 using the scheduled route information 34 sent from the memory part 32 according to the preset task program, without using the manipulating information sent from manipulating device 2.

Moreover, when the operating mode selected in the mode selecting part 71 is the correctable automatic mode, the motion controller 31 uses both the scheduled route information 34 and the manipulating information. Note that, when the operating mode is the correctable automatic mode and the manipulating information has not been sent to the motion controller 31, the motion controller 31 uses only the scheduled route information 34. In more detail, when the operating mode in which the robotic arm 1 is operated is the correctable automatic mode, the motion controller 31 controls the operation of the robotic arm 1 using both the scheduled route information 34 and the manipulating information in response to the reception of the manipulating information while the robotic arm 1 is operating automatically using the scheduled route information 34. Thus, the route scheduled to be traced automatically by the robotic arm 1 based on the scheduled route information 34 is corrected.

The display operating part 72 is used in order to operate the image displayed on the monitor 5. For example, the operator is able to operate the display operating part 72 to enlarge or shrink the image displayed on the monitor 5, change the way to display the scheduled route, etc.

Figure 3:
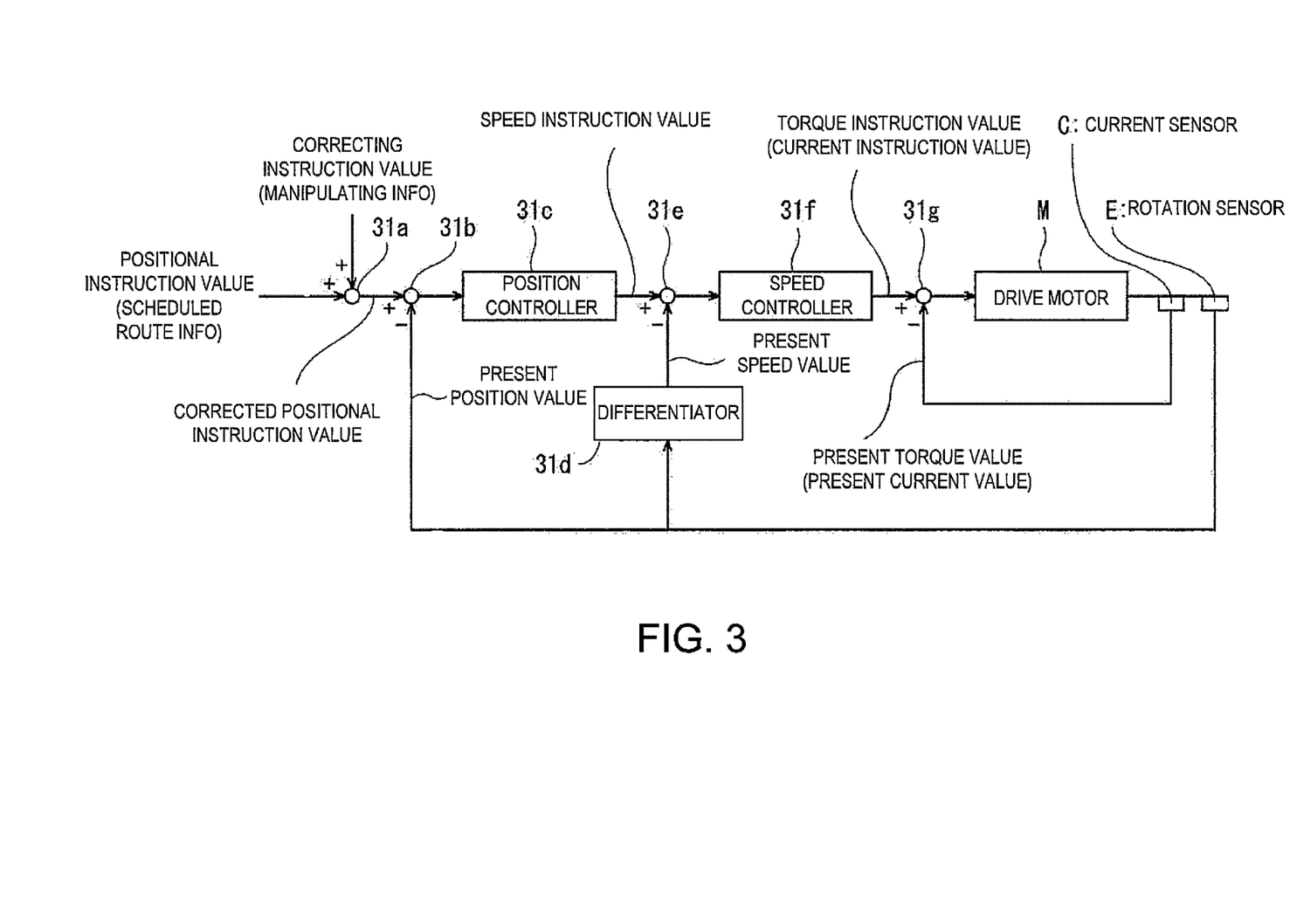
FIG. 3 is a view illustrating one example of a block diagram of a control system of a motion controller illustrated in FIG. 2.

Below, the route correction of the robotic arm 1 when the operating mode in which the robotic arm 1 is operated is the correctable automatic mode is described with reference to FIG. 3. FIG. 3 is a view illustrating one example of a block diagram of a control system of the motion controller 31. In this example, the scheduled route information 34 and the manipulating information are route information which contains, for example, time-series data.

The motion controller 31 includes an adder 31a, subtractors 31b, 31e and 31g, a position controller 31c, a differentiator 31d, and a speed controller 31f, and it controls the rotational position of the drive motor M of the robotic arm 1 according to the instruction value based on the scheduled route information 34 and the instruction value based on the manipulating information.

The adder 31a generates a corrected positional instruction value by adding a correction instruction value based on the manipulating information to the positional instruction value based on the scheduled route information 34. The adder 31a sends the corrected positional instruction value to the subtractor 31b.

The subtractor 31b subtracts a present position value detected by the rotation sensor E from the corrected positional instruction value to generate an angle deviation. The subtractor 31b sends the generated angle deviation to the position controller 31c.

The position controller 31c generates a speed instruction value based on the angle deviation sent from the subtractor 31b by arithmetic processing based on a predefined transfer function and a predefined proportionality coefficient. The position controller 31c sends the generated speed instruction value to the subtractor 31e.

The differentiator 31d differentiates the present position value information detected by the rotation sensor E to generate an amount of change in the rotational angle of the drive motor M per unit time, i.e., a present speed value. The differentiator 31d sends the generated present speed value to the subtractor 31e.

The subtractor 31e subtracts the present speed value sent from the differentiator 31d, from the speed instruction value sent from the position controller 31c to generate a speed deviation. The subtractor 31e sends the generated speed deviation to the speed controller 31f.

The speed controller 31f generates a torque instruction value (electric current instruction value) based on the speed deviation sent from the subtractor 31e by arithmetic processing based on a predefined transfer function and a predefined proportionality coefficient. The speed controller 31f sends the generated torque instruction value to the subtractor 31g.

The subtractor 31g subtracts the present current value detected by the current sensor C, from the torque instruction value sent from the speed controller 31f to generate a current deviation. The subtractor 31g sends the generated current deviation to the drive motor M to drive the drive motor M.

Thus, the motion controller 31 controls the drive motor M to control the robotic arm 1 so that the robotic arm 1 operates along a route corrected from the route related to the scheduled route information 34. Note that, when the operating mode of the robotic arm 1 is the automatic mode, the positional instruction value based on the scheduled route information 34 is sent to the subtractor 31b, and when the operating mode of the robotic arm 1 is the manual mode, the positional instruction value based on the manipulating information is sent to the subtractor 31b.

Figure 4:
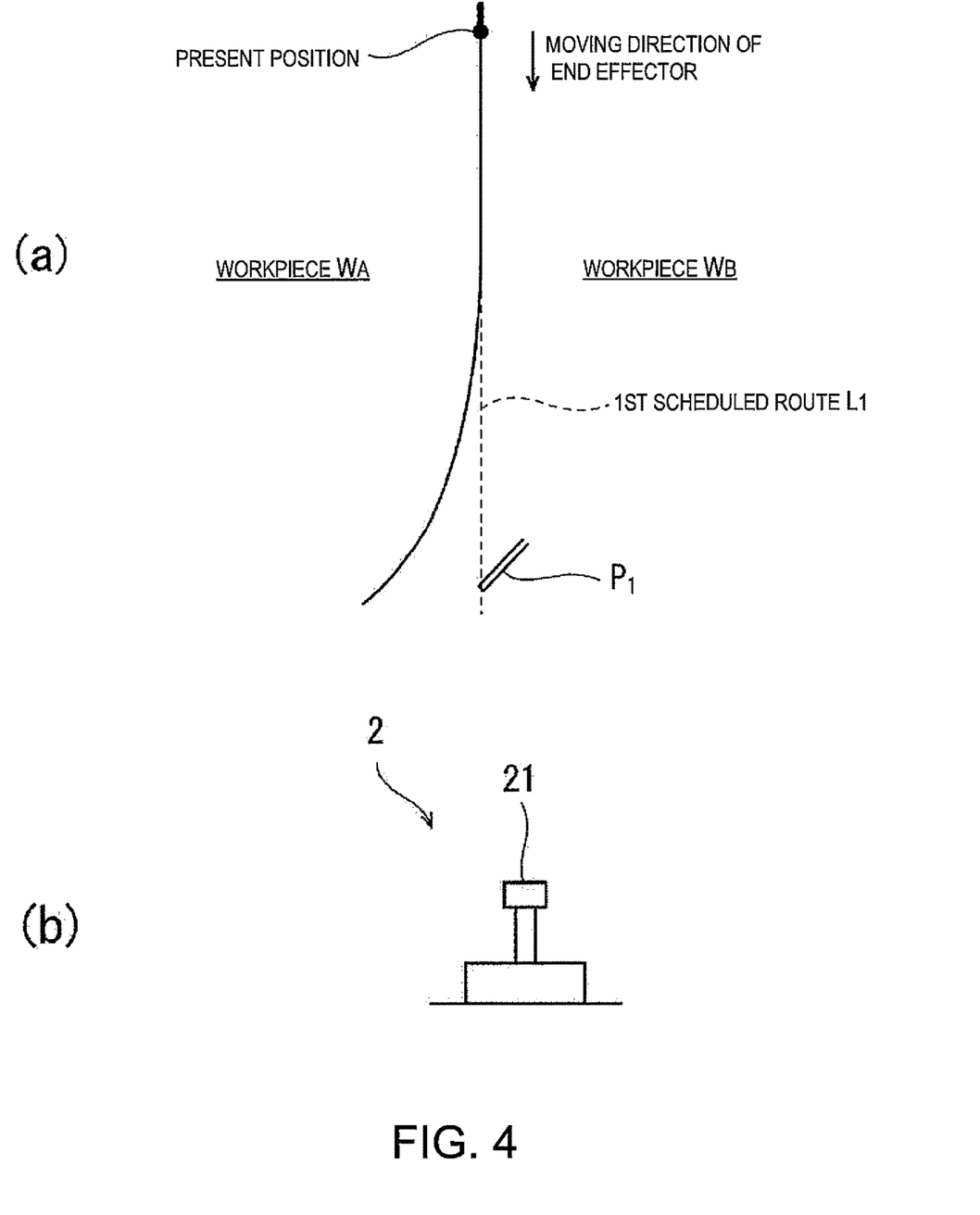
FIG. 4 is a view illustrating a situation of a route correction of a robotic arm by the robot system illustrated in FIG. 1, where (a) illustrates a synthesized image displayed on a monitor, and (b) illustrates a state of a manipulating device.
Figure 5:
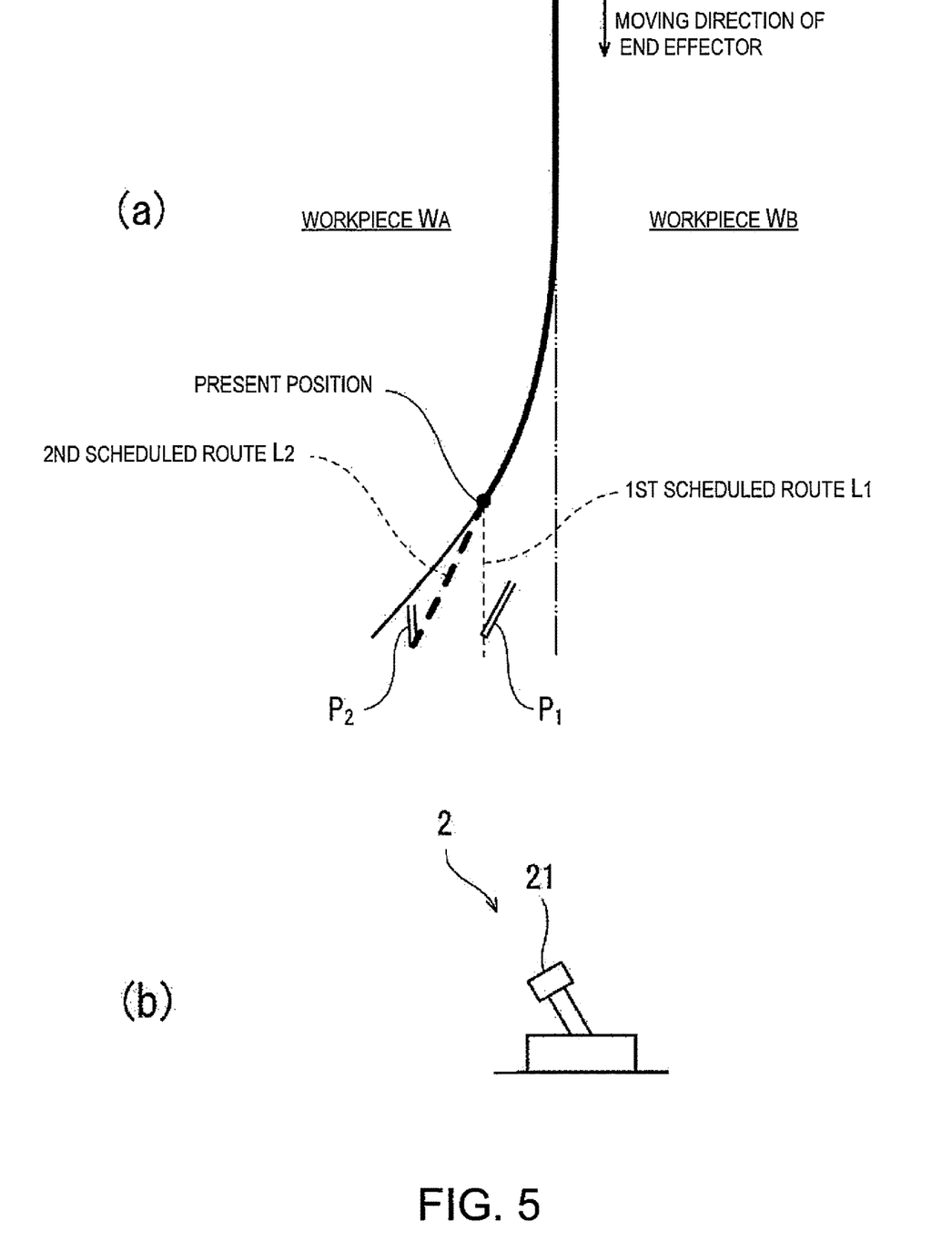
FIG. 5 is a view illustrating a situation of the route correction of the robotic arm slightly after the situation illustrated in FIG. 4, where (a) illustrates a synthesized image displayed on the monitor, and (b) illustrates a state of the manipulating device.

Below, with reference to FIGS. 4 and 5, the route correction of the robotic arm 1 which performs the welding work is described as one example of the route correction of the robotic arm 1. In FIGS. 4 and 5, a situation in which, when the correctable automatic mode is selected as the operating mode in which the robotic arm 1 is operated, the route of the robotic arm 1 (i.e., the route of the end effector 16) is corrected by the manipulating device 2 is illustrated.

FIG. 4(a) illustrates the synthesized image on the monitor 5 at a certain time point. Moreover, FIG. 4(b) illustrates a state of the manipulating device 2 at the same time point. Specifically, FIG. 4(a) illustrates a scheduled route of the end effector 16 and two workpieces W ($W_A$ and $W_B$), which are displayed on the monitor 5. Note that, although the tip-end part of the end effector 16 is displayed on the monitor 5 in an actual case, it is omitted in FIG. 4(a). The two workpieces $W_A$ and $W_B$ are the members to be joined mutually by welding. A thin line illustrated in FIG. 4(a) is a joining part of the two workpieces $W_A$ and $W_B$, and is a part to be welded (hereinafter, referred to as "the joining line"). A thick line illustrated in FIG. 4(a) is the joining part of the two workpieces $W_A$ and $W_B$, and is a part which has already been welded. A black dot which is a joint between the thick line and the thin line illustrated in FIG. 4(a) is a present position of the tip-end part of the end effector 16.

As illustrated in FIG. 4(b), the manipulating device 2 is in the non-manipulated state at the present time point. Thus, as illustrated in FIG. 4(a), the second scheduled route $L_2$ is not indicated in the synthesized image as the scheduled route of the end effector 16 from the present position, but only the first scheduled route $L_1$ is indicated by the thin dashed line. In addition, in FIG. 4(a), the posture image $P_1$ of the end effector 16 when the end effector 16 reaches a given position on the first scheduled route $L_1$ is displayed at this position. As illustrated in FIG. 4(a), the first scheduled route $L_1$ linearly extends downward in this figure from the present position of the tip-end part of the end effector 16. On the other hand, although the joining line extends along the first scheduled route $L_1$ downwardly in this figure from the present position of the tip-end part of the end effector 16, it curves at an intermediate location thereof to the left in this figure. That is, the first scheduled route $L_1$ is deviated from the joining line after the intermediate location of the route. Such a deviation of the first scheduled route $L_1$ from the joining line may be caused, for example, due to variation of the workpieces which are members to be welded.

In order to perform the welding appropriately to the workpieces $W_A$ and $W_B$, an actual route of the end effector 16 needs to be aligned with the joining line. The operator looks at the monitor 5 and checks if the route is to be corrected by the manipulating device 2. Since the first scheduled route $L_1$ of the tip-end part of the end effector 16 is aligned with the joining line, up to the intermediate location of the route from the present position as illustrated in FIG. 4(a), the operator does not manipulate the manipulating device 2 up to the point where the first scheduled route $L_1$ deviates from the joining line. As a result, the motion controller 31 controls the operation of the robotic arm 1 only using the scheduled route information 34 so that the tip-end part of the end effector 16 moves along the scheduled route, i.e., along the joining line.

Moreover, in FIG. 5(a), the synthesized image on the monitor 5 slightly after the time point at which the synthesized image of FIG. 4(a) is indicated is illustrated, and in FIG. 5(b), a state of the manipulating device 2 at the time point at which the synthesized image of FIG. 5(a) is indicated is illustrated. As illustrated in FIG. 5(b), the manipulating device 2 is in the manipulating state at this time point. Thus, as illustrated in FIG. 5(a), in the synthesized image, the first scheduled route $L_1$ is indicated by a thin dashed line and the second scheduled route $L_2$ by a thick dashed line, as the scheduled routes of the end effector 16 from the present position. In FIG. 5(a), the first scheduled route $L_1$ illustrated in FIG. 4(a) is indicated by a two-dot chain line, for reference. Moreover, in FIG. 5(a), a posture image $P_1$ of the end effector 16 when the end effector 16 reaches a given position on the first scheduled route $L_1$ is displayed at this position, and a posture image $P_2$ of the end effector 16 when the end effector 16 reaches a given position on the second scheduled route $L_2$ is displayed at this position.

The operator looks at the monitor 5, and manipulates the manipulating device 2 from a time point at which the tip-end part of the end effector 16 reaches a location where the first scheduled route $L_1$ illustrated in FIG. 4(a) (the route illustrated by the two-dot chain line in FIG. 5(a)) deviates from the joining line, to correct the route of the tip-end part of the end effector 16 so as to be aligned with the joining line, as illustrated in FIG. 5(a). Moreover, the first and second scheduled routes $L_1$ and $L_2$ from the present position are updated as required and are displayed on the monitor 5, as the tip-end part of the end effector 16 moves. Thus, the operator is able to check, as needed, the deviations of the first and second scheduled routes $L_1$ and $L_2$ from the present position, from the route demanded in order to appropriately carry out the work in the captured image (the route along the joining line in this example). Therefore, the operator looks at the monitor 5 and is able to judge of a start timing and a stop timing of manipulation, and the direction of manipulation and the amount of manipulation (a degree of manipulation) of the manipulating device 2. Moreover, the operator looks at the posture images $P_1$ and $P_2$ of the welding torch which is the end effector 16, and is able to judge beforehand whether the angle of the welding torch with respect to the joining line when it traces the scheduled routes $L_1$ and $L_2$ becomes an appropriate angle to perform the welding.

As described above, in the robot system 100 according to this embodiment, since the synthesized image where the scheduled routes of the end effector 16 is synthesized with the captured image where the workpiece W is imaged by the image generator 33 is displayed on the monitor 5, the operator is able to grasp beforehand whether the end effector 16 moves appropriately so as to perform the given work to the workpiece W. In addition, since the route of the end effector 16 during movement is correctable on real time by the manipulating device 2 as the route correcting device, the route of the end effector 16 is corrected at a point where the route correction is necessary, while the operator looks at the synthesized image on the monitor 5.

Thus, in the robot system 100 according to this embodiment, since the point where the route correction is necessary is recognizable from the synthesized image on the monitor 5, it is flexibly adaptable to each work, and since the route correction of the end effector 16 is able to be made by the manipulation only at the necessary part, the operator's labors can be reduced.

Moreover, in this embodiment, the scheduled route of the end effector 16 after the route correction is made by the manipulating device 2 is displayed on the monitor 5. Thus, the operator is able to grasp beforehand whether the end effector 16 moves so as to perform the given work to the workpiece W even after the route correction is made by the manipulating device 2.

Moreover, in this embodiment, since the two scheduled routes $L_1$ and $L_2$ when the manipulating device 2 is not operated from the present time point and when the state where the route correcting device has been operated is maintained from the present time point, are indicated on the monitor 5, the operator is able to judge more accurately about how the manipulating device 2 is to be manipulated.

Moreover, in this embodiment, since the postures of the end effector 16 when the end effector 16 reaches the given positions on the scheduled routes $L_1$ and $L_2$ are displayed on the monitor, it is possible to grasp beforehand whether the end effector 16 takes the posture by which the end effector 16 is capable of appropriately performing the work to the workpiece W when the end effector 16 traces the scheduled routes $L_1$ and $L_2$.

The present disclosure is not limited to the embodiment described above, but various modifications thereof may be possible without departing from the spirit of the present disclosure.

For example, in the embodiment described above, although the image generator 33 updates the scheduled route of the end effector 16 which is synthesized with the captured image based on the present positional information, the image generator 33 may be configured to always display the initial scheduled route indicated in the synthesized image based on the scheduled route information 34, without updating the scheduled route of the end effector 16. Moreover, in the embodiment described above, although the first scheduled route $L_1$ and the second scheduled route $L_2$ are indicated as the scheduled routes synthesized with the captured image, the image generator 33 may be configured to synthesize only one of the first scheduled route $L_1$ and the second scheduled route $L_2$ with the captured image. Moreover, the image generator 33 may not synthesize the posture images $P_1$ and $P_2$ which are the images indicative of the postures of the end effector 16, with the captured image.

Moreover, in the embodiment described above, although the manipulating device 2 is a joystick, it may be a manipulating device 2 having another configuration, and for example, may be a manipulating device 2 provided with a direction key as the manipulating part 21. Moreover, the manipulating device 2 may be comprised of a plurality of devices, and for example, may be comprised of two joysticks.

Moreover, the robot system 100 may be a system utilizing a master-slave type robot, and the manipulating device 2 may be a master arm having a similarity structure to the robotic arm 1 as a slave arm. In this case, when the operating mode in which the robotic arm 1 is operated is the manual mode, the robotic arm 1 operates so as to follow the motion of the master arm 2 which is operated manually. Moreover, in this case, the image generator 33 may be configured to synthesize only the first scheduled route $L_1$ with the captured image.

Moreover, in the embodiment described above, although the robot system 100 is configured to be provided with a single camera 4, the robot system 100 may be provided with a plurality of cameras. For example, the robot system 100 may be configured to be provided with a camera which images the working part of the workpiece W from sideway, in addition to the camera 4 which images the working part of the workpiece W from above. In this case, the image generator 33 may synthesize the scheduled route also with a captured image sent from the camera which images from sideway, and may send the synthesized image to the monitor 5. Both the synthesized image related to the camera 4 which images from above and the synthesized image related to the camera which images from sideway may be displayed on the single monitor 5, or may be displayed on separate monitors, respectively. According to this configuration, since the operator is able to grasp the relation between the workpiece W and the scheduled route three-dimensionally from the plurality of synthesized images, a more appropriate route correction can be performed.

In the embodiment described above, although the input parts, such as the mode selecting part 71 and the display operating part 72, are provided with the single input device 7, they may be provided to separate input devices, respectively. Moreover, the manipulating device 2 and the input device 7 may be configured integrally.

Moreover, in the embodiment described above, although it is configured so that the robotic arm 1 is capable of being operated in the manual mode by manipulating the manipulating device 2, the operating mode in which the robotic arm 1 is operated may not need to include the manual mode. In this case, the manipulating device 2 is utilized as the route correcting device which is used only in the correctable automatic mode, and the mode selecting part 71 may be used in order for the operator to select the operating mode in which the robotic arm 1 is operated from the automatic mode or the correctable automatic mode.

DESCRIPTION OF REFERENCE CHARACTERS

1 Robotic Arm
16 End Effector
2 Manipulating Device (Route Correcting Device)
3 Control Device
31 Motion Controller
32 Memory Part
33 Image Generator
34 Scheduled Route Information
4 Camera
5 Monitor
71 Mode Selecting Part

What is claimed is:

1. A robot system, comprising:
a robotic arm having an end effector configured to perform a work to a work object;
a memory part storing scheduled route information;
a motion controller configured to operate the robotic arm by using the scheduled route information to move the end effector;
a route correcting device configured to generate, by being manipulated, manipulating information to correct a route of the end effector during movement;
a camera configured to image the work object;
an image generator configured to generate a synthesized image by synthesizing a scheduled route of the end effector obtained from the scheduled route information with a captured image sent from the camera; and
a monitor configured to display the synthesized image,
wherein the image generator acquires present positional information on the end effector, and updates, based on the present positional information, one updated scheduled route of the end effector, the one updated scheduled route being synthesized and displayed on the monitor with the capturing image,
wherein the one updated scheduled route of the end effector is a route that the present positional information, when a state where the route correcting device is manipulated is maintained from a present time point, the present time point corresponding to the present position, and
wherein the one updated scheduled route is generated based on the schedule route information, the present positional information, and the manipulating information.

2. The robot system of claim 1,
wherein the image generator further synthesizes with the captured image, another one updated scheduled route that the end effector is scheduled to trace, stalling from the present position, when the route correcting device is not manipulated from the present time point, the another one updated scheduled route being synthesized and displayed on the monitor with the capturing image together with the one updated scheduled route.

3. The robot system of claim 1 wherein the image generator indicates a posture of the end effector when the end effector reaches a given position on the scheduled route.

4. The robot system of claim 2, wherein the image generator indicates a posture of the end effector when the end effector reaches a given position on the scheduled route.

* * * * *